(12) United States Patent
French et al.

(10) Patent No.: US 7,638,632 B2
(45) Date of Patent: Dec. 29, 2009

(54) AROMATIC AND AROMATIC/HETEROAROMATIC MOLECULAR STRUCTURES WITH CONTROLLABLE ELECTRON CONDUCTING PROPERTIES

(75) Inventors: Roger Harquail French, Wilmington, DE (US); Ross Getty, Wilmington, DE (US); Simona Percec, Philadelphia, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 147 days.

(21) Appl. No.: 11/511,934

(22) Filed: Aug. 28, 2006

(65) Prior Publication Data

US 2009/0270627 A1 Oct. 29, 2009

Related U.S. Application Data

(62) Division of application No. 10/722,304, filed on Nov. 25, 2003, now abandoned.

(60) Provisional application No. 60/429,169, filed on Nov. 26, 2002.

(51) Int. Cl.
*C07D 211/66* (2006.01)
*C07D 413/00* (2006.01)
*H01L 35/24* (2006.01)

(52) U.S. Cl. ............... 546/193; 546/269.1; 257/40

(58) Field of Classification Search .............. 546/193, 546/269.1; 257/40, E51.049
See application file for complete search history.

(56) References Cited

U.S. PATENT DOCUMENTS

| | | | | |
|---|---|---|---|---|
| 5,037,916 A | * | 8/1991 | Blumstein et al. | ........... 526/240 |
| 5,233,046 A | * | 8/1993 | Hay et al. | ................. 548/257 |
| 6,303,733 B1 | * | 10/2001 | Lau et al. | .................. 528/169 |
| 6,430,511 B1 | | 8/2002 | Tour et al. | |

FOREIGN PATENT DOCUMENTS

EP 0521360 B1 1/1993
WO W002/35580 * 5/2002

OTHER PUBLICATIONS

S.M. Dirk et al, Accoutrements of a molecular computer:switches, memory components and allegator clips, 2001, p. 5019-5121.*
Bossenbroek et al, In teractions and Chemistry of 1,8-bis-(phenylethylnyl)naphthalene and 1,8-bis(1-alkyynyl) naphthalenes,J. Am.Chem. Soc.,1969, 91(2),p. 371-379.*
S. J. Tour, Molecular Electronics. Synthesis and Testing of Components, Acc. Chem. Res., vol. 33, pp. 791, 2000.
J. Chen et al., Large On-Off Ratios and Negative Differential Resistance in a Molecular Electronic Device, Science, vol. 286, p. 1550,1999.
Wong et al., Fabrication and Transport Properties of Single-Molecule-Thick Electrochemical Junctions JACS, 2000, vol. 122, pp. 5821-5840.
Collier et al., Electronically Configurable Molecular-Based Logic Gates, Science, vol. 285, Jul. 16, 1999.
Whiteford et al., Molecular Architecture via Coordination, J. Am. Chem. Soc., vol. 119, pp. 2524-2533, 1997.
Ciana et al., Synthesis of 1,4-Bis(4-Pyridyl)butadiyne, J. Heterocycl. Chem. 1984, pp. 607-608.

* cited by examiner

*Primary Examiner*—Taylor Victor Oh

(57) ABSTRACT

Aromatic and aromatic/heteroaromatic molecular structures with controllable electron conducting properties are derived from the incorporation of electron active substituents in selective positions.

1 Claim, 11 Drawing Sheets

X-Ray Crystal Structure of 1,4 -Bis(4-Pyridyl)Butadiyne

X-Ray Crystal Structure of 1,4-Bis(4-Pyridyl)Butadiyne

X-Ray Crystal Structure of 4-Ethynyl(Pyridine)-4'-Ethynylphenyl-5'-Nitro-1Pyridine X-Ray Crystal Structure of 4-Ethynyl (1, 2 - dicyanobenzene) -4'-Ethynylphenyl -1(4, 5 - dicyanobenzene)

X-Ray Crystal Structure of 1-Thioacetyl-4(4'-Fluoro-1'-(Ethynyl)Phenyl)Benzene

X-Ray Crystal Structure of 4-Ethynyl(2-Fluoro-Cyanobenzene)-4'-Ethynylphenyl-1(2-Fluoro-Cyanobenzene)

Index of refraction (n) and the extinction coefficient (k) versus wavelength lambda (λ) in units of nanometers for the self assembled molecules of Example 9, PETB.

Index of refraction (n) and the extinction coefficient (k) versus wavelength lambda (λ) in units of nanometers for the self assembled molecules of Example 10, pF-PETB.

Index of refraction (n) and the extinction coefficient (k) versus wavelength lambda (λ) in units of nanometers for the self assembled molecules of Example 11, 3N-PETB.

Index of refraction (n) and the extinction coefficient (k) versus wavelength lambda (λ) in units of nanometers for the self assembled molecules of Example 12, 3-PETB.

Index of refraction (n) and the extinction coefficient (k) versus wavelength lambda (λ) in units of nanometers the self assembled molecules of Example 13, 2F2CN3B.

Index of refraction (n) and the extinction coefficient (k) versus wavelength lambda (λ) in units of nanometers for the self assembled molecules of examples 9, PETB, 10, Pf-PETB, 11, 3N-PETB, 12, 3-PRTB and 13, 2F2CN3B.

AROMATIC AND AROMATIC/HETEROAROMATIC MOLECULAR STRUCTURES WITH CONTROLLABLE ELECTRON CONDUCTING PROPERTIES

This application claims the benefit of U.S. Provisional Application 60/429,169, filed Nov. 26, 2002.

FIELD OF INVENTION

The invention is directed to the preparation of novel aromatic and aromatic/heteroaromatic molecular structures with controllable electron conducting properties which can form self-assembled layers on metal or other substrates, and can be used in molecular scaled electronic devices.

BACKGROUND

The expanding commercial interest in the generation of small nano-scale electronic devices highlights a need for the generation of a new class of conductive molecules that are functionalized for use in nano-electronic device fabrication. However, the discovery of new conductive molecules for this is fraught with difficulty. For example, little is known about the specifics of how conductive molecules work. Additionally, it is difficult to connect conductive molecules to electrodes and even more difficult to perform conductivity measurements on single molecules. In addition to the difficulties in construction, the design of new molecules possessing useful properties is hampered by the lack of a facile method for correlating the effects of optical transitions to electronic molecular properties. Once a structure is designed, the synthesis, purification and growth of single crystals of molecules as large as these is not easily accomplished. Typically, multistep separations are required. Finally, the coupling of different aromatic and heteroaromatic building blocks is difficult to achieve because substituted structures are prone to side reactions and long reaction times.

In spite of these difficulties a number of conductive molecules have been synthesized. For example, Tours et al (U.S. Pat. No. 6,430,511 (S. J. Tour, *Acc. Chem. Res.*, 33, 791, 2000) teaches the assembly of molecular structures consisting of phenylene/ethynylene units and the measurement of the resistance/conductivity of a self-assembled monolayer deposited on a pattern of electrodes. Very few of these structures have been demonstrated to display distinct negative differential resistance (NDR) (increased resistance with increasing driving voltage) and then only under specific conditions, mostly at low temperatures.

Additionally several groups (J. Chen, et al, *Science*, Vol 286, pg. 1550, 1999; E. W. Wong et al, *JACS*, 2000, 122, 5821-5840; have synthesized conducting molecules and measured the negative differential resistance behavior and conductivity of a monolayer of this material between two surfaces. C. P. Collier et al, (*Science*, vol. 285, 16 Jul. 1999) have synthesized rotaxanes and catenanes molecules, made monolayers of these molecules using Langmuir-Blogett techniques, and demonstrated resonant tunneling current flow derived from the reversible inter-conversion between two different states.

The above listed references teach the synthesis of useful compounds, however do not address the need for functionalized molecules specifically adapted for facile nano-device fabrication.

Applicants have met the stated need with the design and synthesis of novel aromatic and aromatic/heteroaromatic having specific substituents useful for the incorporating these molecules into nano-electronic devices.

SUMMARY OF THE INVENTION

The invention provides new aromatic/heteroaromatic conducting molecules useful in nano-electronic devices and methods of making the same. The molecules of the invention may additionally comprise barrier groups (—CH$_2$, cyclic, etc.) and are versatile, allowing for the assembly of molecular components (possessing different terminal groups) in two or three dimensions.

Accordingly the invention provides a conducting molecule according to Formula I, II, or III:

$$R-C\equiv C-R \quad \text{I}$$
$$R-C\equiv C-C\equiv C-R \quad \text{II}$$
$$R-C\equiv C-B-C\equiv C-R \quad \text{III}$$

wherein R is independently selected from the group consisting of:

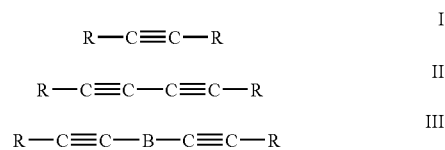

wherein A is independently selected from the group consisting of H, a C$_1$-C$_6$ alkyl group, F, —CN, and —S—C(=O)—CH$_3$, wherein at least one of F, —CN, and —S—C(=O)—CH$_3$ is present;

and B is selected from the group consisting of:

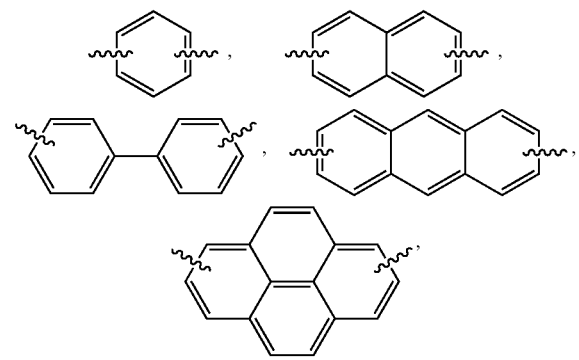

-continued

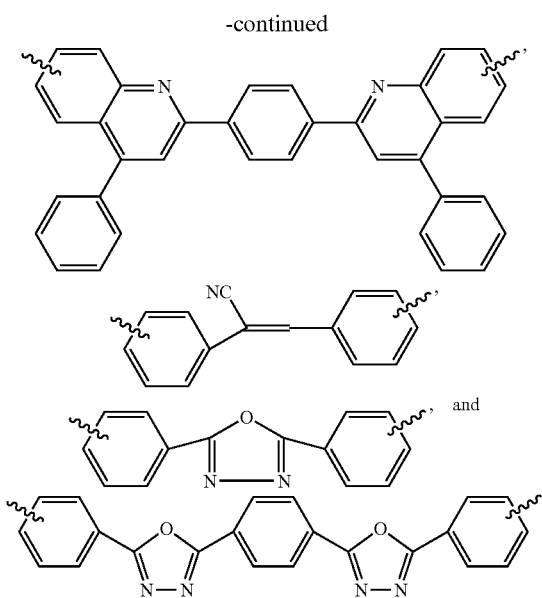

wherein B is optionally substituted with H, a $C_1$-$C_6$ alkyl group, F, —CN, —$NO_2$, and —S—C(=O)—$CH_3$.

Additionally the invention provides a molecular based memory system, molecular wire, or molecular switch, comprising the composition of the invention.

In another embodiment the invention provides a process for synthesizing a supramolecular structure comprising the steps of:
 (a) providing a conducting molecule of the invention;
 (b) providing a suitable substrate;
 (c) contacting the conducting molecule of (a) with the substrate of (b) wherein the conducting molecule is immobilized on the substrate;
 (d) contacting the immobilized conducting molecule of (c) with a redox or photochemical reagent under conditions wherein the immobilized conducting molecule is activated; and
 (e) contacting the activated conducting molecule with the conducting molecule of step (a) wherein molecular addition takes place and a supramolecular structure is formed.

In an alternate embodiment the invention provides a supramolecular structure synthesized by a process of the invention as well as sensors comprising the same.

DETAILED DESCRIPTION OF THE INVENTION

Figure 1:
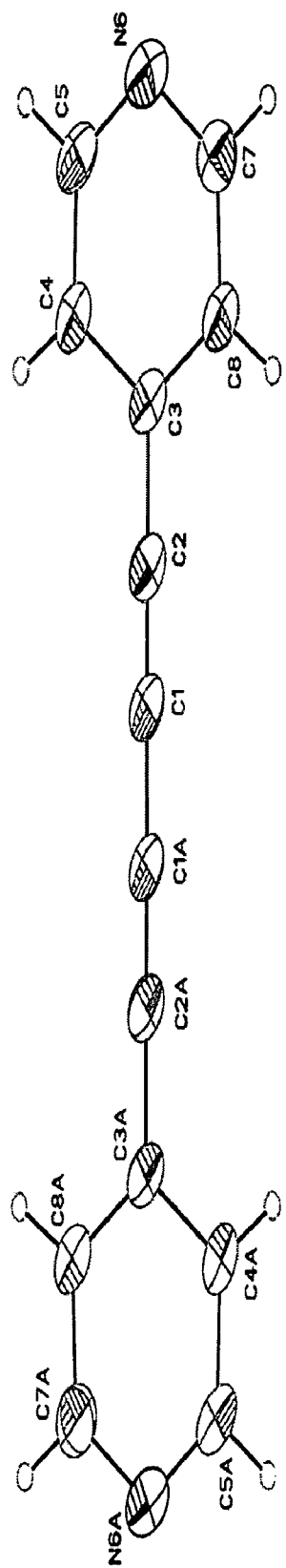
FIG. 1 shows the x-ray crystal structure of 1,4-bis(4-pyridyl)butadiyne), example 1.

This invention relates to the design, synthesis, self-assembly and processing in the solid state of organic molecules with controllable electron conducting, semiconducting, insulating properties and/or switch characteristics derived from the presence of appropriate electron active substituents placed in selective positions of the aromatic and heteroaromatic structures.

The present compounds advance the art in that they are robust enough to allow for molecular manipulation at different temperatures and conditions. The present compounds may be used in the synthesis of three-terminal devices, logic switches and other nano-electronic devices.

Additionally the compounds of the invention can function as active elements in electronic devices such as in SAMs for random-access-memory devices where data can be written, read and erased, or in sensors. Similarly, single molecules can be used as molecular wires and/or molecular switches. Wires and switches are the most basic components of memory and logic devices and components comprised of the present materials will play a critical role in reducing the size of today's computer circuits.

The following definitions and abbreviations may be used for the interpretation of the claims and the specification.

"SAM" is the abbreviation for "self assembled monolayer".

"SA" is the abbreviation for "self assembly".

As used herein, "alkyl" means an alkyl group containing up to 6 carbon atoms. Common examples of such alkyl groups include methyl, ethyl, propyl, isopropyl, butyl, s-butyl, isobutyl, pentyl, neopentyl, hexyl, and cyclohexyl. The alkyl group may be linear, branched, or cyclic.

Within the context of the molecular formulae illustrated herein, the attachment points of the groups designated as "R" and B" are indicated by ⌇, and unless specifically attached to a position on the ring the point of attachment can be at any open position of the designated ring.

The term "conducting molecule" means any molecule that has the ability to conduct a flow of electrons from one end of the molecule to the other.

The term "supramolecular structure" means a complex of at least two, and preferably a plurality of conducting molecules. Supramolecular structures of the invention may be formed through the self-assembly of conducting molecules.

As used herein the term "molecular based memory system" refers to a molecule or set of molecules that have the ability to alter its conductivity by storing electrons.

The term "molecular wire" means any molecular structure that allows the flow of electrons from one end to the other end of the structure. In a preferred embodiment molecular wires of the invention will comprise at least two terminals for contacting additional components of a nano-electronic device.

The term "molecular switch" is used interchangeably with "controllable wire" and refers to a molecular structure where the electron flow can be turned on and off on demand. In a preferred embodiment a molecular switch will both switch and amplify the current. In some embodiments molecular switches can have a number of different terminals, where the two terminal and three terminal conformations are typical. In the three terminal case, one terminal functions as the source of the current while the second terminal functions as the drain. The third terminal in the switch functions as the gate and acts to vary the electrical conductivity of the device. Assemblies of molecular wires and switches can be interconnected to produce complex circuitry for use as logic or memory or interconnection devices. (see for example M. Reed and J. Tour, Scientific American, June 2000, pages 86-93 and Molecular *Electronics: Science and Technology*, Edited by A. Aviram and M. Ratner. Annals of the New York Academy of Sciences, vol. 852; 1998.)

The invention provides conducting molecules having substituents strategically placed within the molecule which affect the electrical conducting properties of the molecule.

Design and Synthesis of Conducting Molecules

It is one object of the present invention to design and prepare conducting molecules in such a manner so as to control the electronic conduction properties of the resulting compounds. A number of possible building blocks for preparation are possible, where aromatic and aromatic/heteroaromatic molecules are preferred. These may be linked together in configurations in which π low energy orbitals are delocalized from one end to the other end of the molecule by incorporating specific types of electron-active groups as substituents in selected positions.

The aromatic and or aromatic/heteroaromatic structures of the present invention are synthesized via cross-coupling reactions of halogenated aromatic compounds with terminal aromatic acetylenes as illustrated in the examples. Various electron active, withdrawing (F, $CF_3$, $SO_2CF_3$) and donating ((N $(CH_3)_2$, $N(C_2H_5)_2$) groups are used to substitute different positions of the aromatic and heteroaromatic rings in order to vary the conduction properties and/or achieve controlled response with voltage fluctuations. The ends of these molecules are individually functionalized with groups such as SH, pyridine, CN, SCN, etc. to promote the absorption and self-assembly (SA) on metal surfaces including Au, Cu, Pd, Pt, Ni, Al, $Al_2O_3$, etc. The ability of these groups to promote molecular self-assembly has been well documented (see for example George M. Whitesides; Scientific American, September 1995). The SA may be achieved either by microcontact printing or flooding the metal surfaces or both.

In some instances it will be useful to further functionalize the molecules of the invention to enhance their ability to bind to various substrates. For example functional end groups such as SCN, $NH_2$ can be utilized as binding sites for biological and other molecules. Biological materials that can be bond in this manner include but are not limited to nucleic acid (DNA, RNA and peptide nucleic acids (PNA)), proteins, lipids and complex macromolecules comprising combinations of the same. End groups of this sort are referred to herein as "alligator clips" or "molecular fragments" for their ability to link up with other molecules. The use of alligator clip functionalization will permit the construction of hybrid organic/inorganic/biological devices. For example it is expected that molecules having these functional groups could interact with DNA by intercalating one or more aromatic groups between base pairs of the double helix. Such molecules are expected to have applications in biosensors or other biomedical devices as described for example by Lokey et al., Journal of the American Society, 119, pp. 7202-7210, 1997

In other applications binding to various metals will be useful. In these applications the use of co-absorption of two types of molecules, one electron-donor and the other electron acceptor to the metal, is expected to lead to the formation of ordered SA surface structures with both molecules in the same surface unit cell. The molecules of the invention combine the ability to electron conduct/insulate and/or switch with the ability to build self-assembled mono- or multilayers and supramolecular objects that are neither mono nor layers and are thus particularly useful in the construction of nano-electronic devices.

Several aids are available in the design of the molecules of the invention. For example changes in optical absorption characteristics derived from structural variations of molecular self-assemblies monitored by spectroscopic ellipsometry (SE) can be correlated with interband transitions and used to directly demonstrate the control of electronic properties. These techniques may be used to determine the effectiveness of various substituents to alter electrical conducting properties in the molecules of the invention.

Synthesis of Conducting Supramolecules

Once the conducting molecule is designed it may be assembled into molecular conglomerates or supramolecules having conducting properties. Redox chemistry and photochemistry make use of the alligator clip functionality and can be used to build up supramolecular objects sequentially.

For example a first molecule (M1) comprising a plurality of functional "alligator clip" groups may be redox reacted (by gas exposure or photoexcitation) resulting in the disassociation of the clips. A second or third molecule (M2 or M3) may then be contacted with the reacted M1 where self-assembly will take place. Additional units may be added to the complex in a similar fashion by repeating the process. The sequential nature of this molecular construction is particularly effective in the construction of supermolecular switches and sensing devices.

Once assembled it may be useful to immobilize these supramolecular structures on a solid support in a patterned or unpatterned fashion as components in nano-electronic devices. It is contemplated that at least two and preferably a plurality of these supramolecular structures may be laid down on a substrate. Suitable substrates for this purpose include, but are not limited to silicon wafers, synthetic polymer supports, such as polystyrene, polypropylene, polyglycidylmethacrylate, substituted polystyrene (e.g., aminated or carboxylated polystyrene; polyacrylamides; polyamides; polyvinylchlorides, etc.), glass, agarose, nitrocellulose, nylon, nickel grids or disks, carbon supports, aminosilane-treated silica, polylysine coated glass, mica, and semiconductors such as Si, Ge, and GaAs.

When a conducting molecule is fixed to the surface of a substrate it may be contacted with a redox of photochemical reagent which results in the activation of the molecule. By "activation" it is meant that a conducting molecule is treated in a manner whereby it is disposed to reacting with other conducting molecules for the generation of a supramolecular structure. The activated molecules are then contacted with additional conducting molecules and supramolecular structures are sequentially constructed.

The conductive molecules of the invention are expected to have metallic (ohmic) and in some cases semiconductive behavior. These behaviors lend themselves to the use of these compounds both as interconnects and as actual electronic devices (e.g., switches, logic gates). In one instance, the conductive molecules are expected to be able to link nanometer scale electronic devices together permitting the fabrication of high-density electronic circuits. It is contemplated that it will be possible to array these compounds in a crossed arrangement, where the distance between adjacent molecules can be controlled by the potential difference between them, then the array could be used as a non-volatile memory device. Examples of such construction is described by Rueckes T. et al. (2000). Science 289, 94-97 for carbon nanotubes. Semiconducting molecules could find use in 3-terminal gated devices which can be used directly as switches, amplifiers or logic gates. Other possible applications include point sources for emission in field-emission display devices and as conductive inclusions in conductive coatings.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Unless otherwise specified below all chemical reagents were obtained from the Sigma Chemical Co. (St. Louis, Mo.) or Aldrich (Milwaukee, Wis.).

The meaning of abbreviations is as follows: "h" means hour(s), "min" means minute(s), "sec" means second(s), "d" means day(s), "mL" means milliliters, "L" means liters.

Example 1

Preparation of 1,4-Bis(4-Pyridyl)Butadiyne

Reagents Used Include:
4-Ethynylpyridine hydrochloride: 97%, Mw=139.58, Mp 150° C., Aldrich: 53, 092-1
  Diethyl Ether: Mw=74.12 d=0.713, Bp 35-36° C.
  Triethylamine: Mw=101.19 d=0.726, Mp −115° C., Bp 88.8° C.,
  Aldrich:
  47, 128-3
  Copper (I) Chloride: Mw-98.99, Mp 430° C., Aldrich: 22, 962-8
  Oxygen: Mw=32, Mp-218° C., Bp-183° C., Aldrich: 29,5604
  4-Ethynylpyridine: Mw=103.1237, Mp 95-96° C.,
  Pyridine: Mw=79.10, D=0.983, Bp 115-115° C. Aldrich: 27, 097-0

This compound was synthesized by oxidative coupling of 4-ethynyl pyridine (freshly prepared from its hydrochloride form as described below) in pyridine in the presence of copper (I) chloride according to the following reaction scheme:

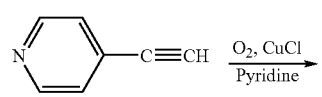

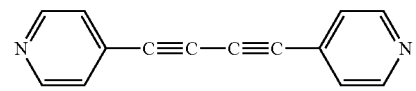

Crystallization from carbon tetrachloride gave colorless plates with the following structure as determined from X-ray diffraction data.

Crystal Data: $C_{14}H_8N_2$, from carbon tetrachloride, colorless, irregular plate, ~0.450×0.330×0.020 mm, monoclinic, P21/n, a=3.759 (6) Å, b=22.95 (3) Å, c=5.801 (8) Å, beta=90.02 (3)°, Vol=500.4 (13). The crystal structure is shown in FIG. 1.

A modified procedure for the Sonagashira coupling methodology was used as described in J. A. Whiteford et al., *J. Am. Chem. Soc.*, 119, 2524-2533, (1997) and L. D. Ciana et al., *J. Heterocycl. Chem.* 1984, 607-608. Free 4-ethynylpyridine was obtained by reacting 4.19 g (30.0 mmol) of 4-ethynylpyridine hydrochloride with 4.18 mL (30.0 mmol) of triethylamine in 50 mL of diethyl ether at room temperature over night. 2.6 g (25.2 mmol) 4-ethynylpyridine, 50 mL (621 mmol) pyridine, and 0.2 g (2.02 mmol) copper (I) chloride were charged into a 250 mL Schlenk flask with a stir bar. Oxygen was then bubbled into the solution via a lecture bottle of $O_2$ connected to a ⅛ inch Teflon® tubing. The reaction was stirred for 45 minutes at room temperature and pressure. The precipitate appeared after 10 minutes. The precipitate was then filtered and washed with water and dried in a dry box in the absence of light. The resulting compounds were subjected to several crystallization steps until pure crystals were obtained. The crude product can also be purified by sublimation (15 torr and 70° C.) or by recrystallization using carbon tetrachloride, which yields colorless plates of the product.

Other compounds were synthesized or can be synthesized by Sonogashira reaction using palladium (0)/CuI catalyzed cross coupling of aromatic halides with terminal acetylenes according to the following general reaction scheme:

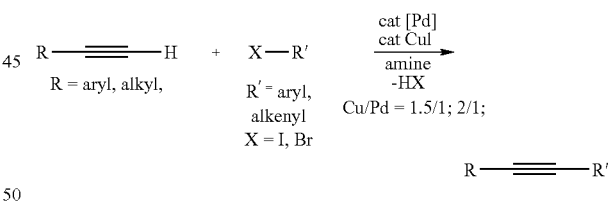

The coupling reactions were carried out in a heavy-walled flask. A catalytic system such as: bis-(dibenzylideneacetone palladium)(0), Pd(dba)$_2$ (2 mol %), triphenylphosphine (Pd catalyst/ligand=1:1), copper (I) iodide and triethylamine and the aromatic halide, carefully handled in a dry box and introduced in the flask. The flask was evacuated and back-filled with nitrogen several times prior the addition of the aromatic terminal acetylene. All these procedures were carried out in a dry box. The flask was then sealed and moved to a regular hood and heated if necessary to 70° C. for 24 hours with stirring. The solvent was evaporated under vacuum and the residue was purified by flash chromatography. The resulting product was recrystallized from appropriate solvents. When necessary the products were subjected to several crystallization steps until pure crystals were obtained.

Example 2

Preparation of 4-Ethynyl(Pyridine)-4'-Ethynylphenyl-5'-Nitro-1-Pyridine

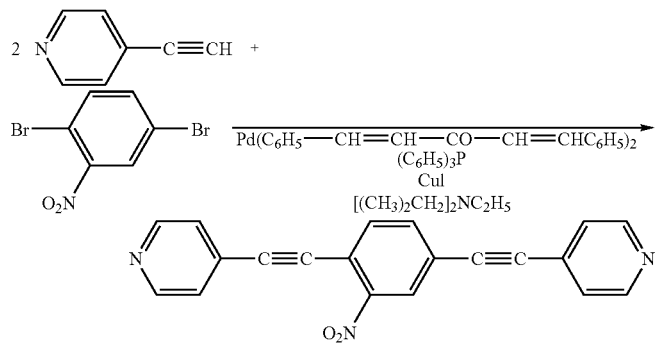

Figure 2:
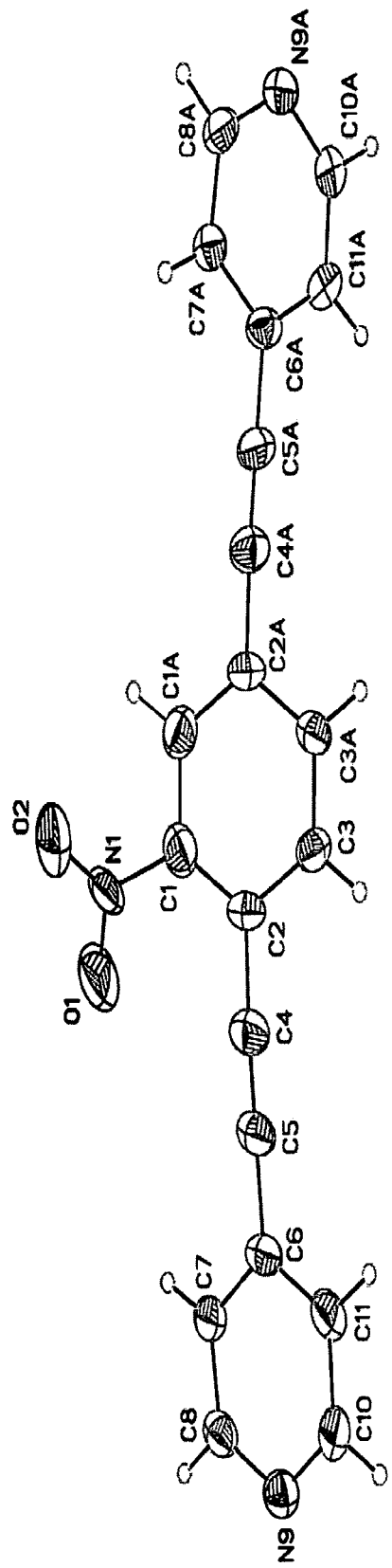
FIG. 2 shows the x-ray crystal structure of 4-ethynyl(pyridine)-4'-ethynylphenyl-5'-nitro-1 pyridine, example 2.

This compound was synthesized as described above in Example 1. Crystallization from ethanol gave colorless needles with the following structure as determined from X-ray diffraction data. The crystal structure is shown in FIG. 2. It can be seen that the mean plane of the outer rings forms an angle of 28.3 degrees with the inner ring.

Crystal Data: $C_{20}H_{11}N_3O_2$, from ethanol, colorless, needle, ~0.220×0.020×0.020 mm, monoclinic, C2/c, a=16.351 (3) Å, b=11.659 (3) Å, c=9.2685 (19) Å, beta=117.706 (5)°, Vol.=1564.3 (6) Å3, Z=4, T=−100° C., Formula weight=325.32, Density=1.381 mg/m3, μ(Mo)= 0.09 $mm^{-1}$.

Example 3

Preparation of 4-Ethynyl(Pyridine)-4'-EthynylBiphenylene-1-Pyridine

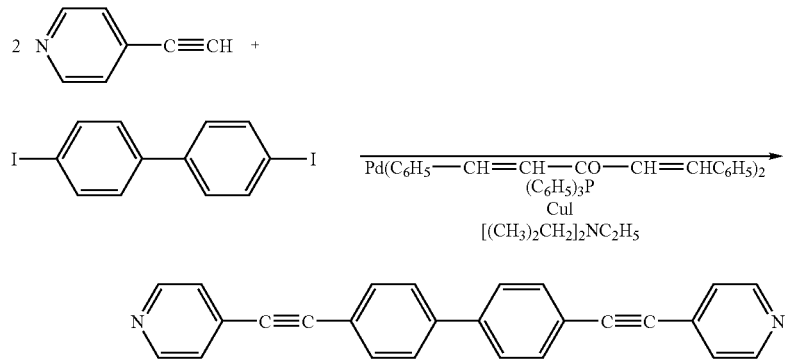

4-Ethynyl(pyridine)-4'-ethynylbiphenylene-1-pyridine can be synthesized according to the procedure outlined in Example 1 via the reaction scheme shown above.

Example 4

Preparation of 4-Ethynyl(Pyridine)-4'-EthynylNaphthalene-1-Pyridine

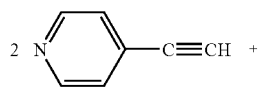

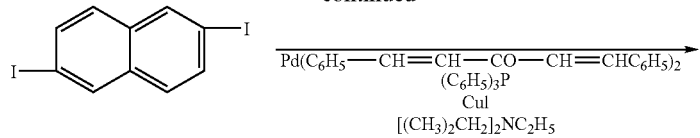

-continued

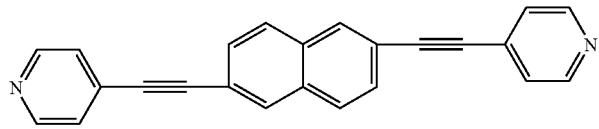

15

4-Ethynyl (1,2-dicyanobenzene) 4'-ethynylphenyl-1(4,5-dicyanobenzene) can be synthesized according to the procedure outlined in Example 1 via the reaction scheme shown above.

Example 5

Preparation of 4-Ethynyl (1,2-dicyanobenzene)-4'-Ethynylphenyl-1(4,5-dicyanobenzene)

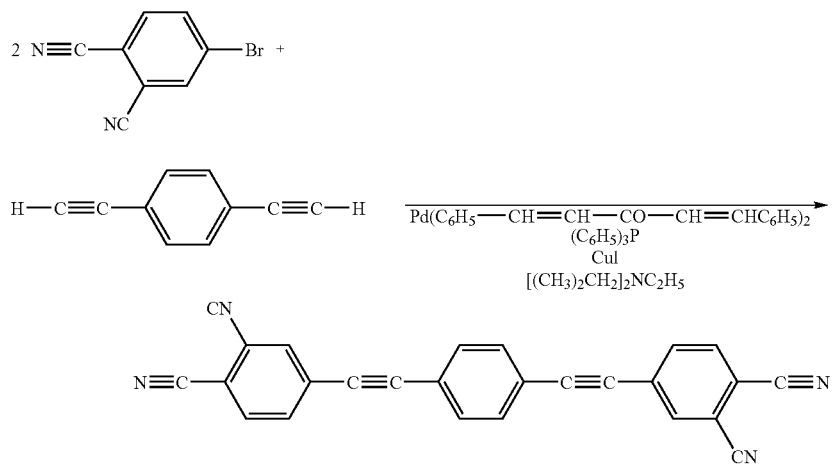

4-Ethynyl (1,2-dicyanobenzene)-4'-ethynylphenyl-1(4,5-dicyanobenzene) was synthesized according to the procedure outlined in Example 1 via the reaction scheme shown above.

Figure 3:
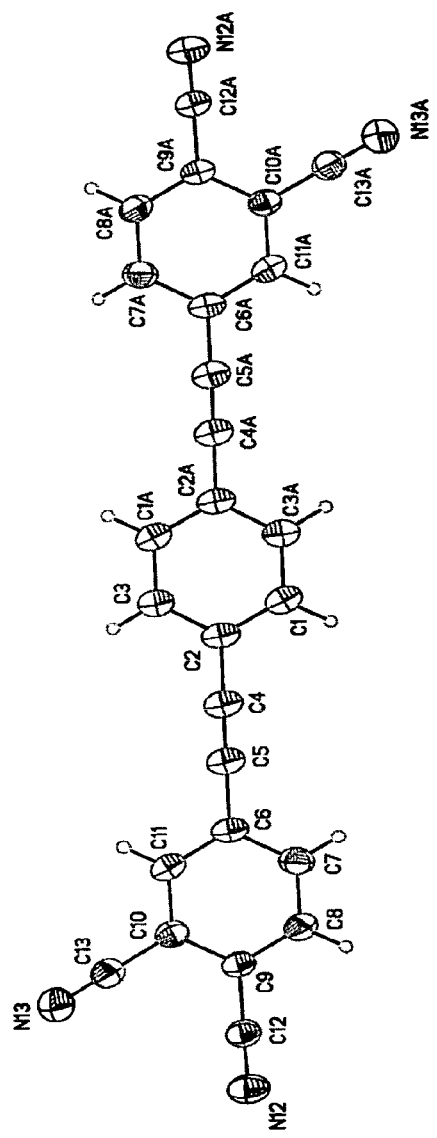
FIG. 3 shows the x-ray crystal structure of 4-ethynyl (1,2-dicyanobenzene) 4'-ethynylphenyl-1(4,5-dicyanobenzene), example 5.

Crystallization from methylene chloride gave colorless needles with the following structure as determined from X-ray diffraction data. The crystal structure is shown in FIG. 3.

Crystal Data: $C_{26}H_{10}N_4$, from $CH_2Cl_2$, colorless, needle, ~0.300×0.040×0.040 mm, monoclinic, P21/n, a=6.5903 (13) Å, b=12.823 (3) Å, c=11.659 (2) Å, beta=100.32 (3)°, Vol.=969.3 (3) Å3, Z=2, T=−100° C., Formula weight=378.38, Density=1.296 mg/m$^3$, μ(MO)=0.08 mm$^{-1}$.

Example 6

Preparation of 1-Ethylpyrene Thioacetyl Benzene

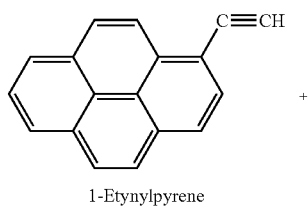

1-Etynylpyrene

+

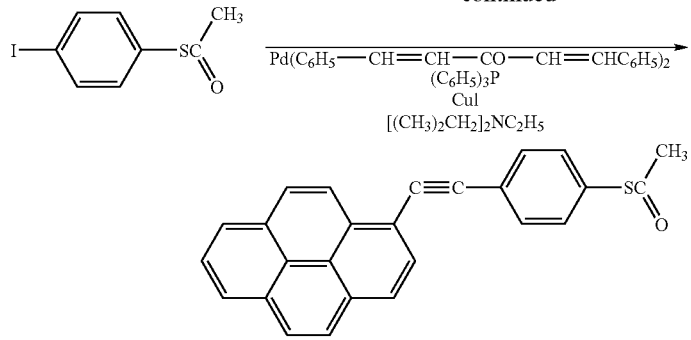

1-Ethylpyrene thioacetyl benzene can be synthesized according to the procedure outlined in Example 1 via the reaction scheme shown above.

Example 7

Preparation of 1-Ethylpyrene-4-(2-Fluoro-Cyanobenzene)

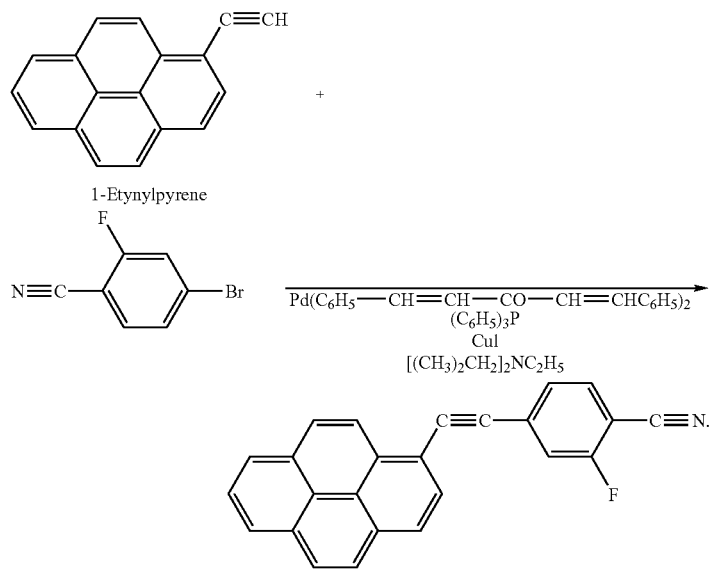

1-Ethylpyrene-4-(2-fluoro-cyanobenzene) can be synthesized according to the procedure outlined in Example 1 via the reaction scheme shown above.

Example 8

Preparation of 1-Ethylpyrene-4-(Pentafluorbenzene)

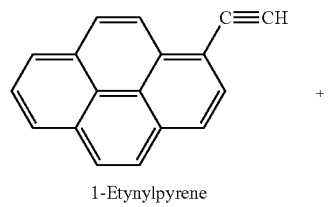

1-Etynylpyrene

+

-continued

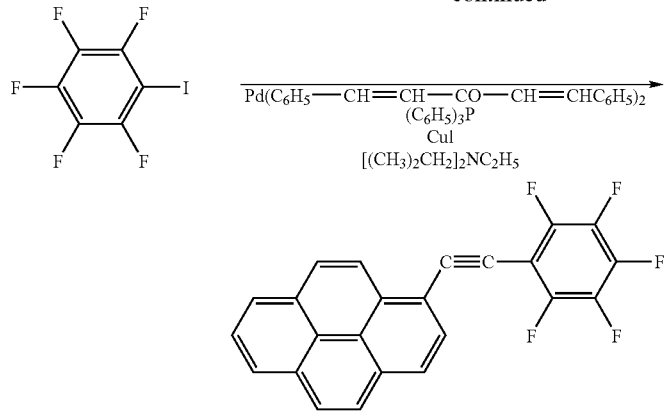

1-Ethylpyrene-4-(pentafluorbenzene) can be synthesized according to the procedure outlined in Example 1 via the reaction scheme shown above.

Example 9

Preparation of 1-Thioacetyl-4(4'-Fluoro-1'-(Ethynyl)Phenyl)Benzene: pF-PETB

Figure 4:
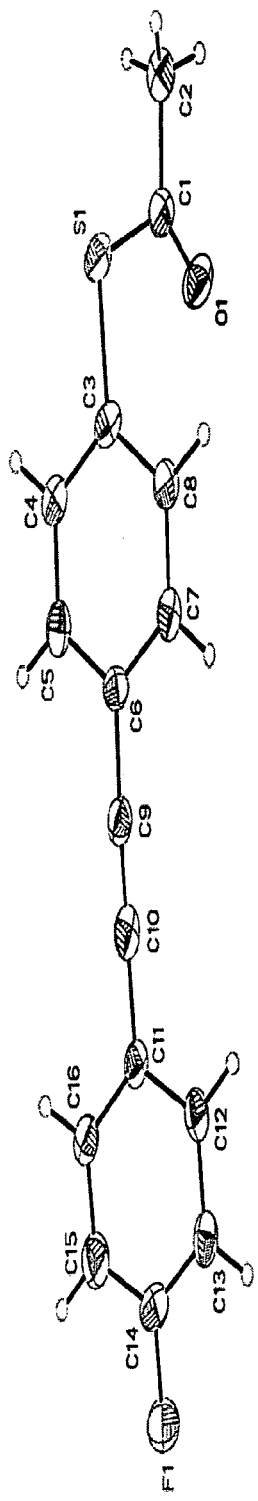
FIG. 4 shows the x-ray crystal structure of 1-thioacetyl-4 (4'-fluoro-1'-(ethynyl)phenyl)benzene, example 9.

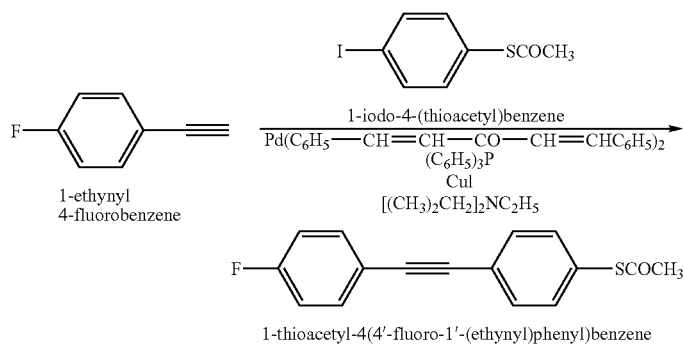

pF-PETB was synthesized according to the procedure outlined in Example 1 via the reaction scheme shown above. The compound was recrystallized from ethanol, to give colorless, thin needle crystals whose structure as determined from X-ray diffraction analyses is shown in FIG. 4:

Crystal Data: $C_{16}H_{11}F\ O\ S$, from ethanol, colorless, thin needle, 0.220×0.040×0.010 mm, monoclinic, C2/c, a=24.998 (5) Å, b=9.442 (2) Å, c=11.627 (3) Å, beta=111.318 (4)°, Vol=2556.5 (10) Å3, Z=8, T=−100° C., Formula weight=270.31, Density=1.405 mg/m$^3$, μ(Mo)=0.25 mm$^{-1}$.

Example 10

Preparation of 4-ethynyl(2-fluoro-cyanobenzene)-4'-ethynylphenyl-1(2-fluoro-cyanobenzene): 2F2NC3B This aromatic ethynylene compound was synthesized by palladium (0)/CuI catalyzed cross coupling reaction of 1,4 diethynyl benzene and 4-bromo-2-fluorobenzonitrile according to the scheme shown below:

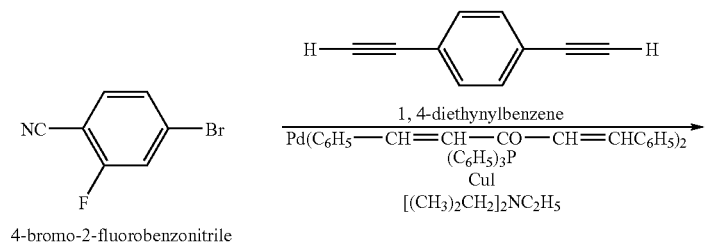

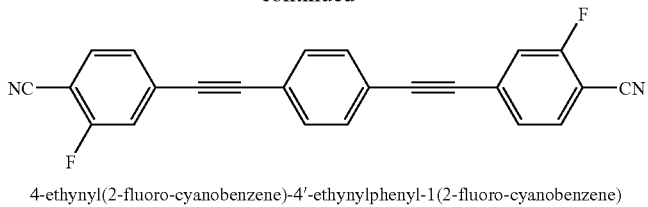

4-ethynyl(2-fluoro-cyanobenzene)-4′-ethynylphenyl-1(2-fluoro-cyanobenzene)

Figure 5:
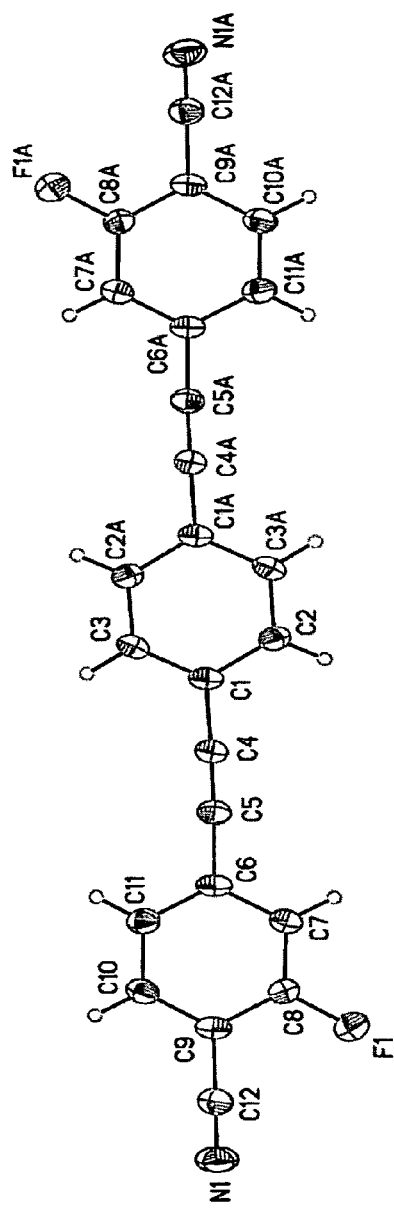
FIG. 5 shows the x-ray crystal structure of 4-ethynyl(2-fluoro-cyanobenzene)-4'-ethynylphenyl-1 (2-fluoro-cyanobenzene), example 10.
Figure 6:
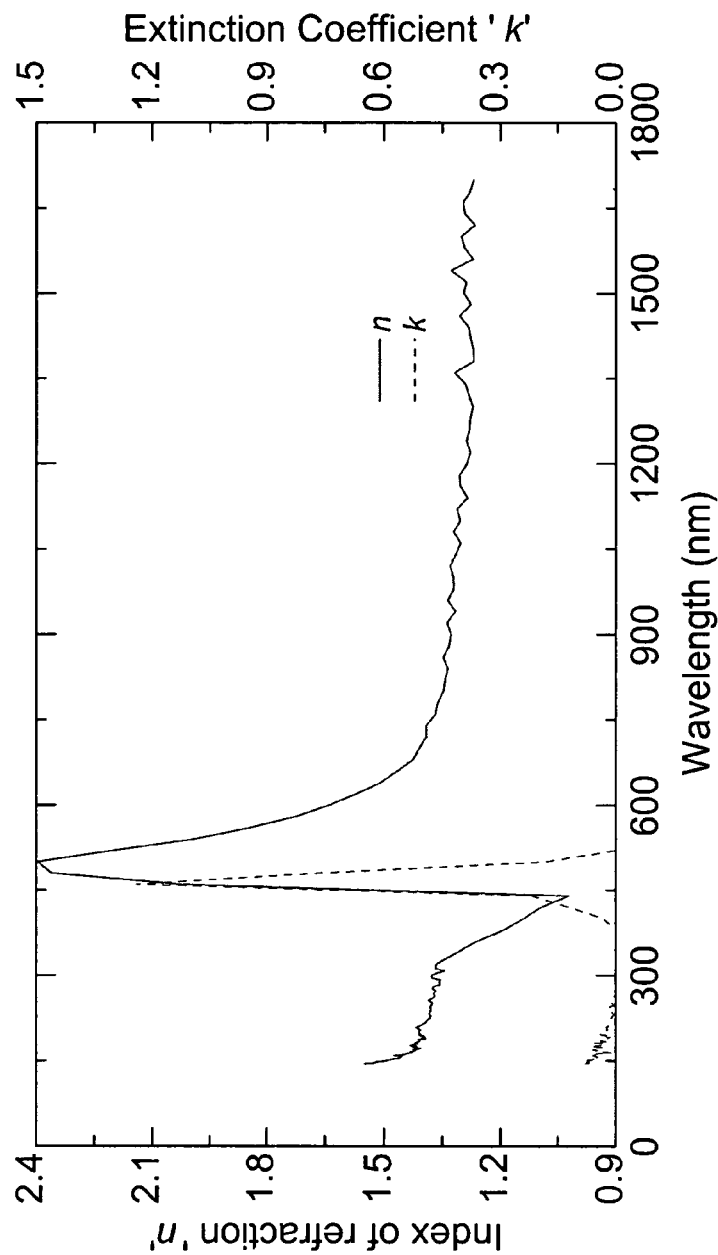
FIG. 6 is a graph of the index of refraction (n) and the extinction coefficient (k) versus wavelength lambda (λ) for the self assembled molecules of example 9, PETB.
Figure 7:
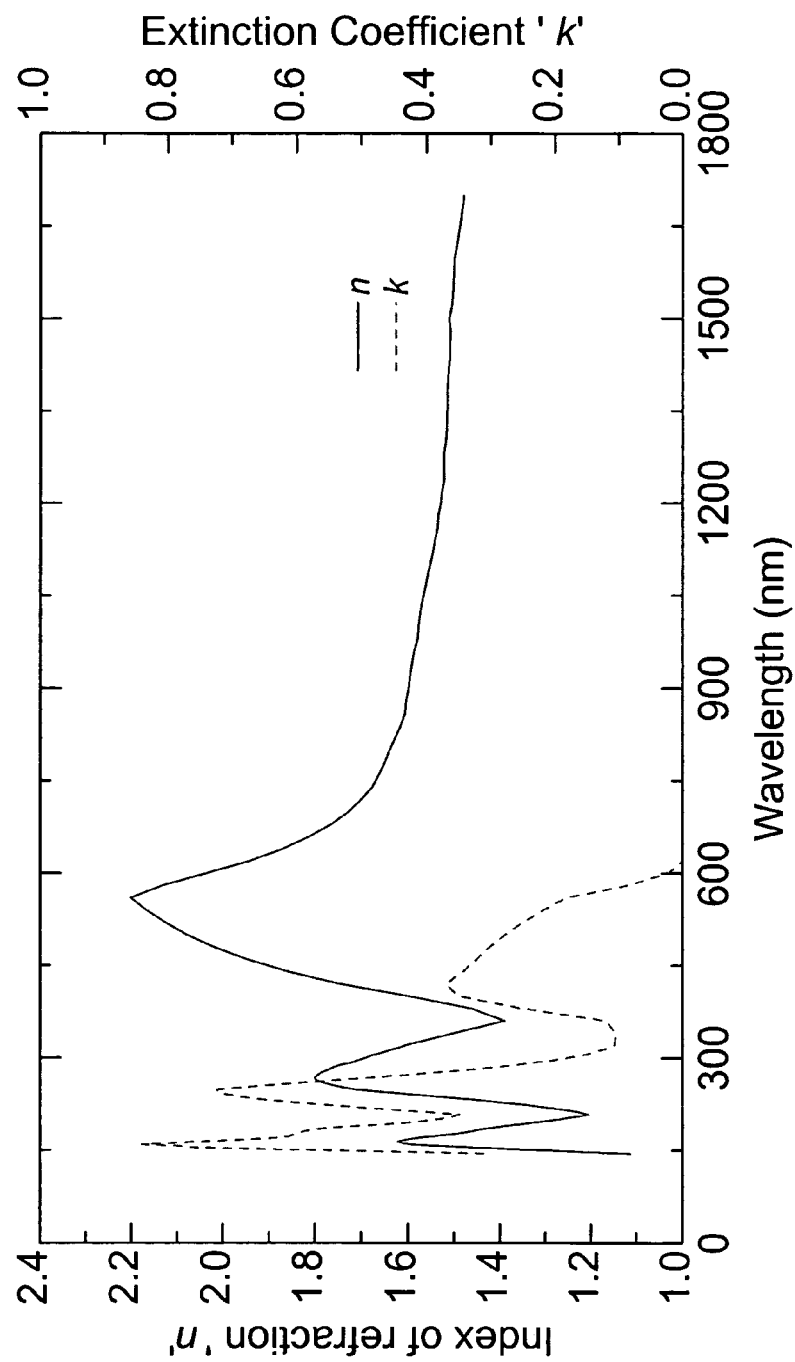
FIG. 7 is a graph of the index of refraction (n) and the extinction coefficient (k) versus wavelength lambda (λ) for the self assembled molecules of example 10, pF-PETB.
Figure 8:
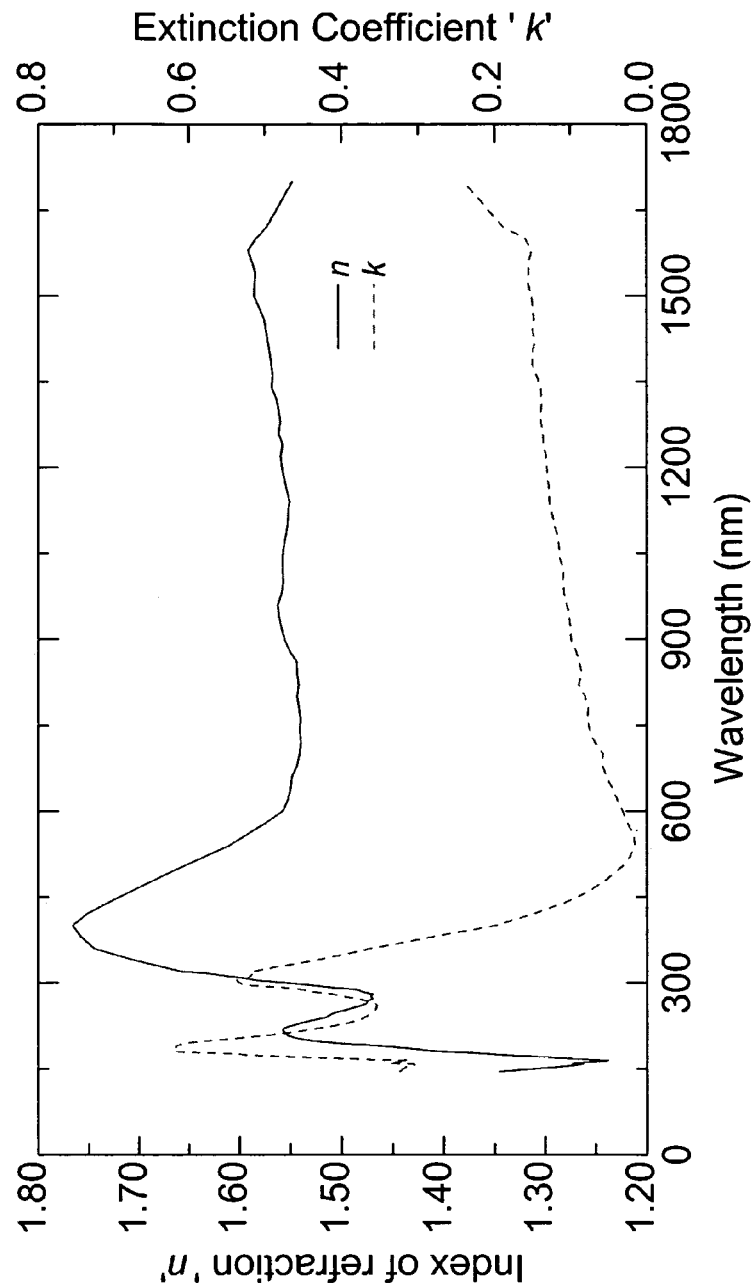
FIG. 8 is a graph of the index of refraction (n) and the extinction coefficient (k) versus wavelength lambda (λ) for the self assembled molecules of example 11, 3N-PETB.
Figure 9:
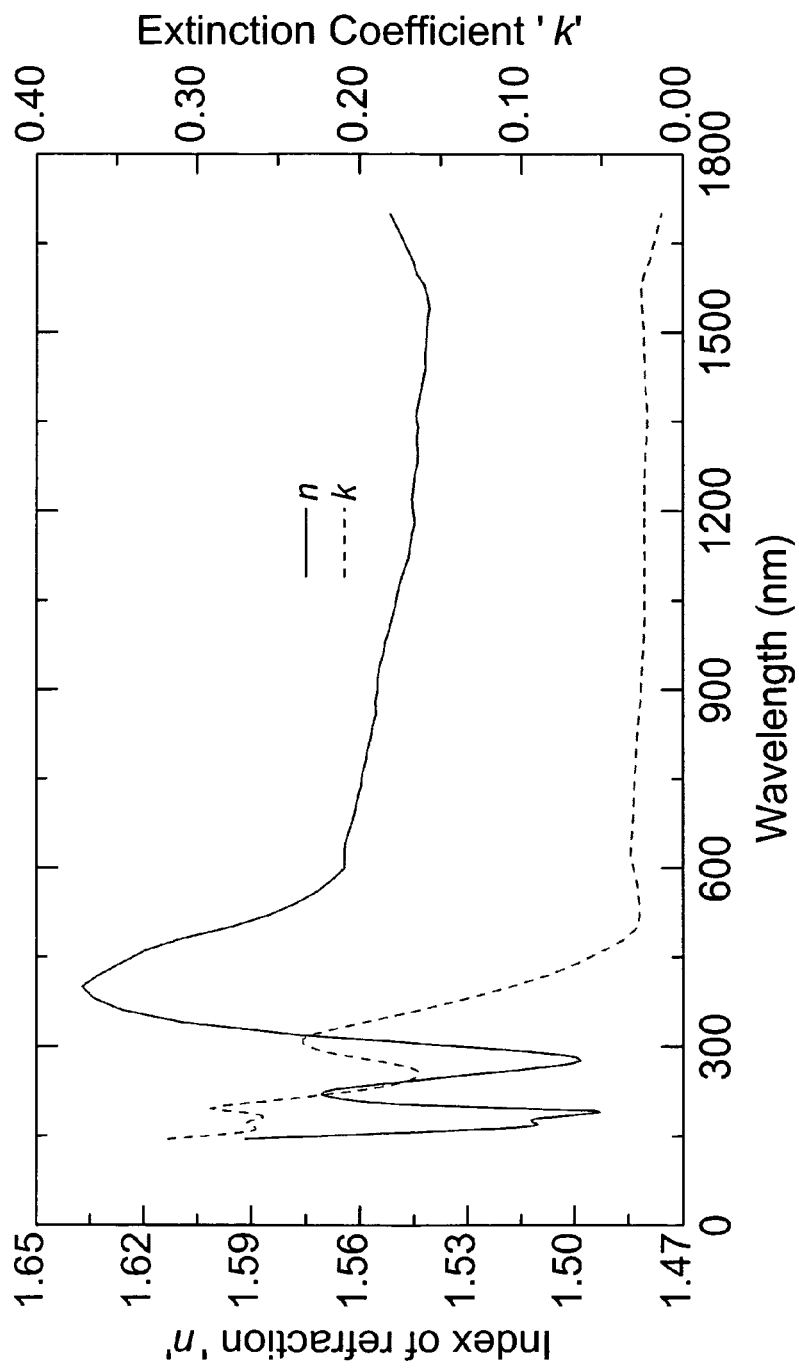
FIG. 9 is a graph of the index of refraction (n) and the extinction coefficient (k) versus wavelength lambda (λ) for the self assembled molecules of example 12, 3-PETB.
Figure 10:
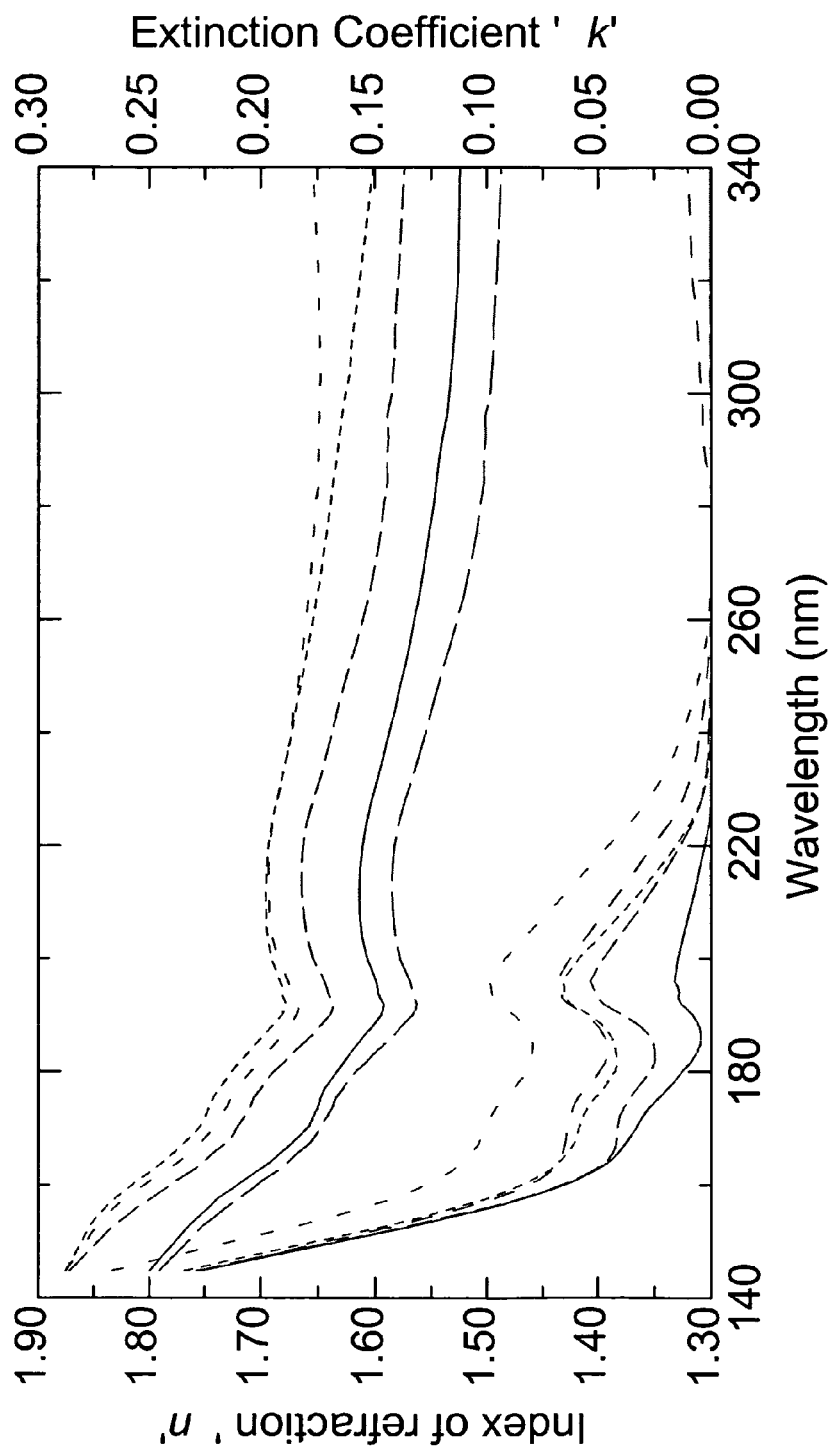
FIG. 10 is a graph of the index of refraction (n) and the extinction coefficient (k) versus wavelength lambda (λ) the self assembled molecules of example 13, 2F2CN3B.
Figure 11:
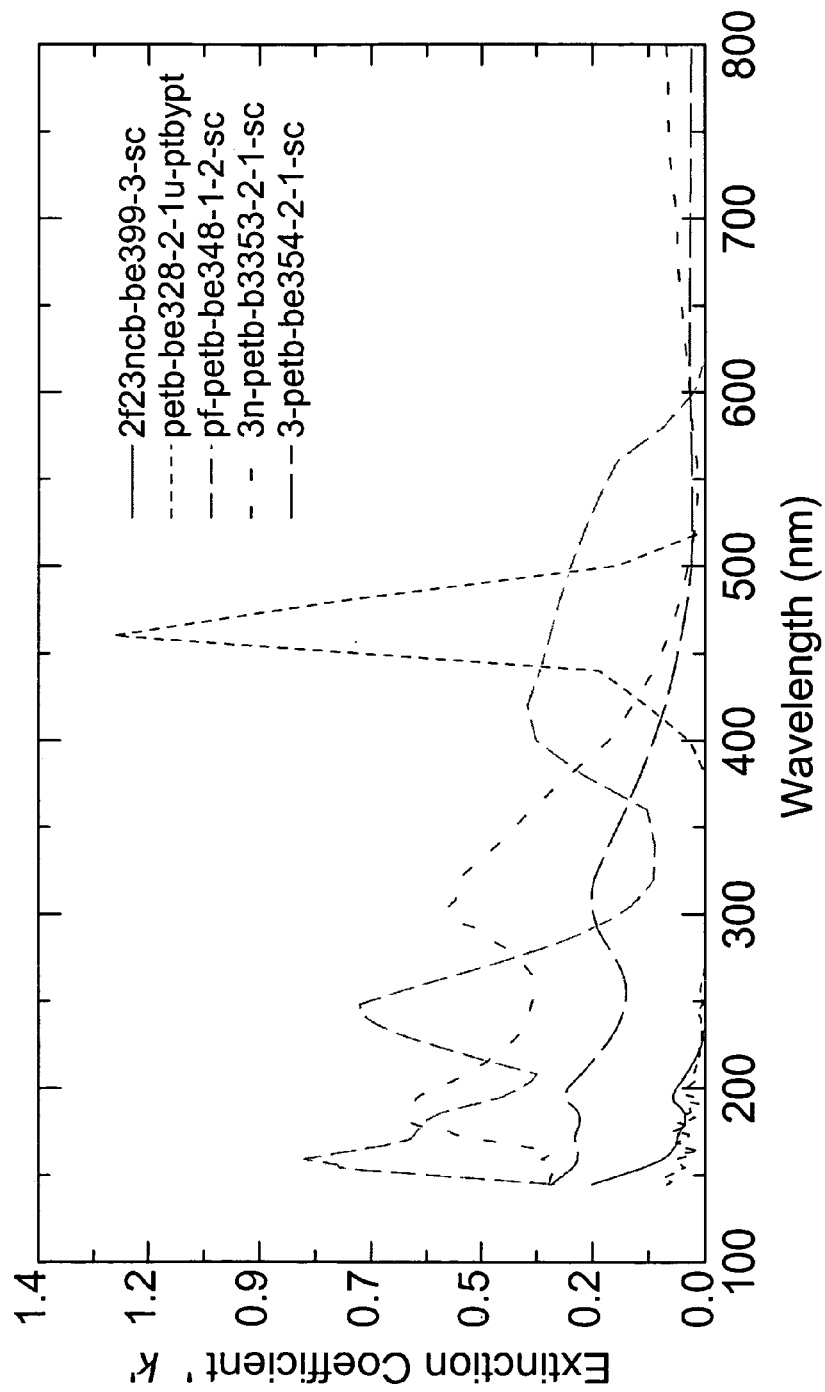
FIG. 11 is a graph comparing the index of refraction (n) and the extinction coefficient (k) versus wavelength lambda (λ) for the self assembled molecules of examples 9, PETB, 10, Pf-petb, 11, 3N-PETB, 12, 3-PRTB and 13, 2F2CN3B.

The resulting compound was subjected to several crystallization steps until pure crystals were obtained. The structure of crystals was determined from X-ray diffraction analysis. The crystal structure as determined from X-ray diffraction analyses is shown in FIG. 5.

Crystal Data: $C_{24}H_{10}F_2N_2$, from hexane/dichloromethane, colorless, plate, ~0.500×0.450×0.030 mm, monoclinic, P21/c, a=14.600 (12) Å, b=5.101 (4) Å, c=11.553 (9) Å, beta=99.926 (14)°, Vol=847.5 (12) Å3, Z=4, T=−100.° C., Formula weight=182.17, Density=1.428 mg/m³, μ(Mo)= 0.10 mm⁻¹.

Example 11

Prophetic

Several heterostructures can be synthesized according to the reaction schemes shown below.

Conjugated heterostructure from 2,2′-(p-phenylenebis(6-bromo-4-phenylenequinoline) and 4-ethynyl pyridine:

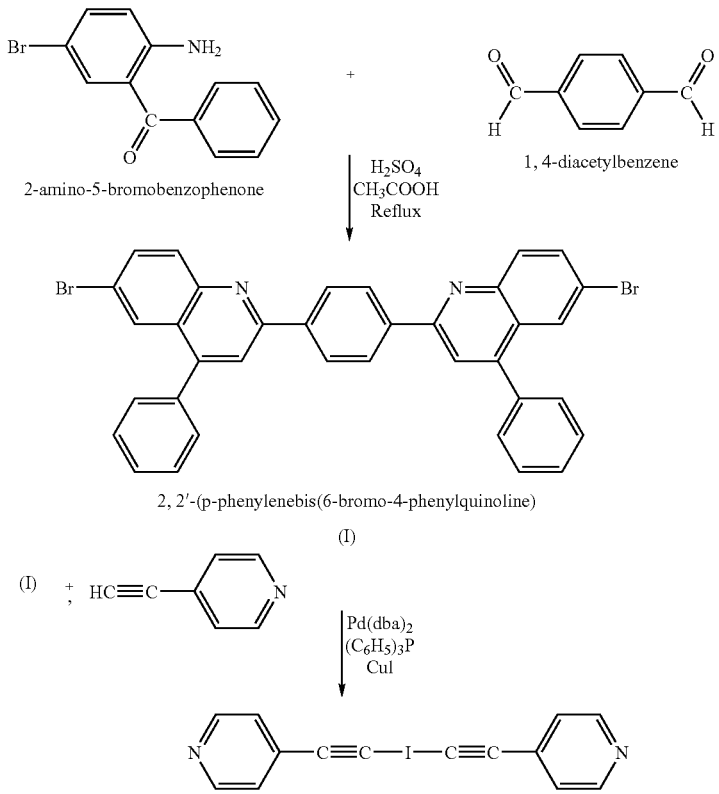

Conjugated heterostructure from 1,2-bis(bromophenyl1-cyanovinylene and 4-ethynyl pyridine:

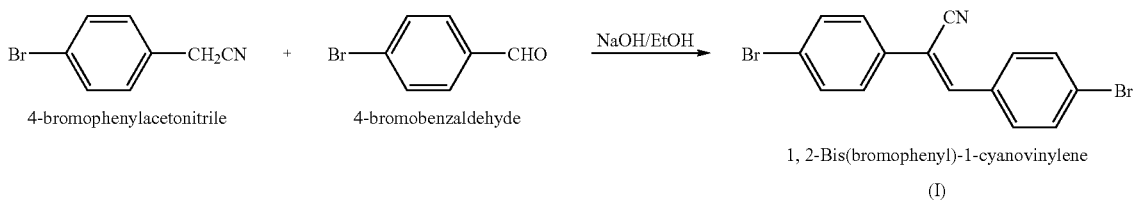

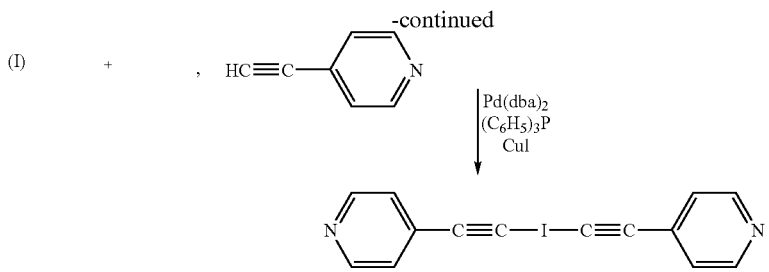
Conjugated heterostructure from 2,5(4-bromophenyl)1,3,4-oxadiazole and 4-ethynyl pyridine:
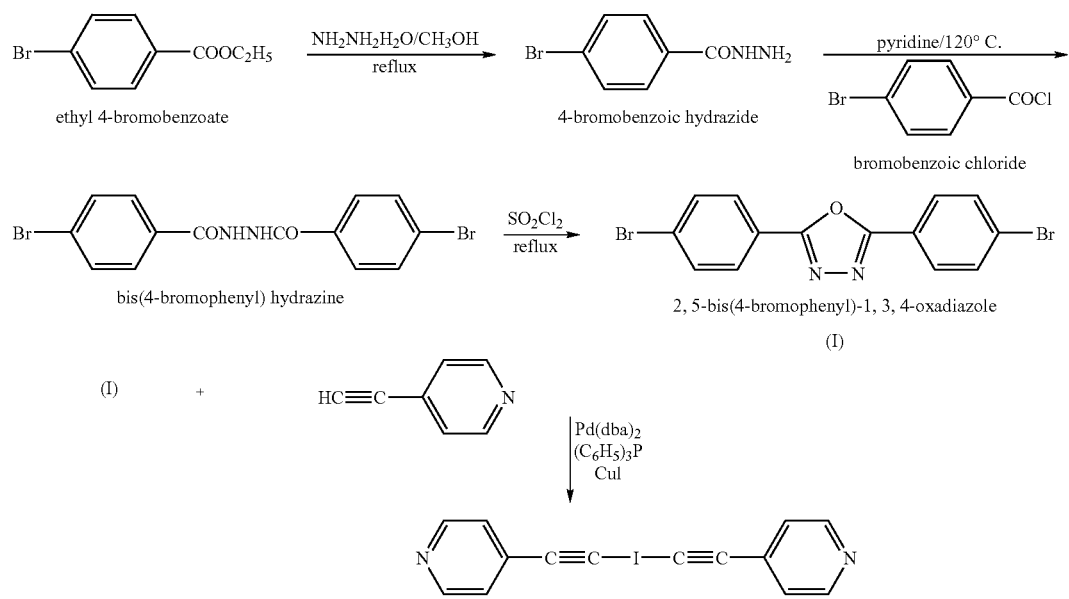
Conjugated heterostructure from 1,4-bis[4-bromophenyl) 1,3,4-2-yl]benzene-oxadiazole and 4-ethynyl pyridine:
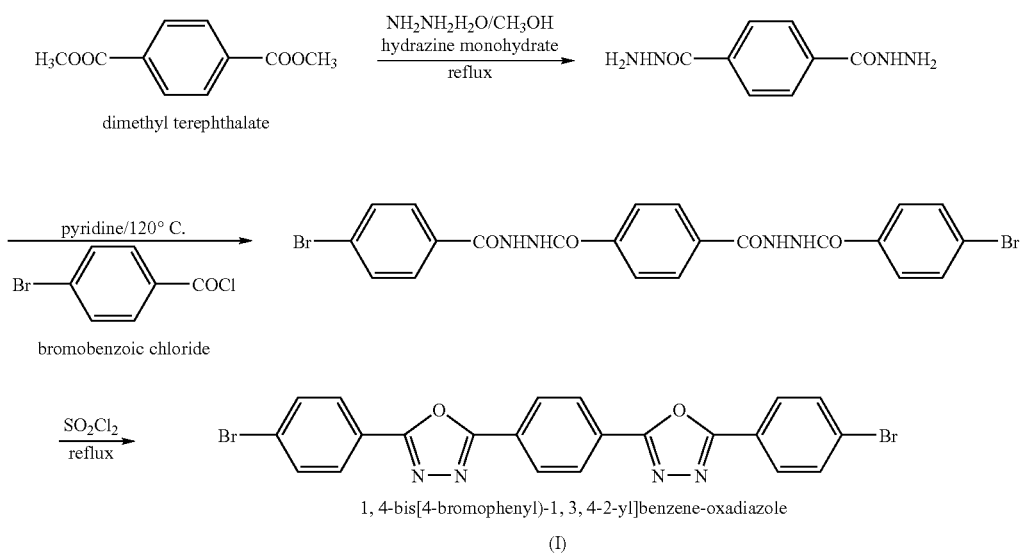

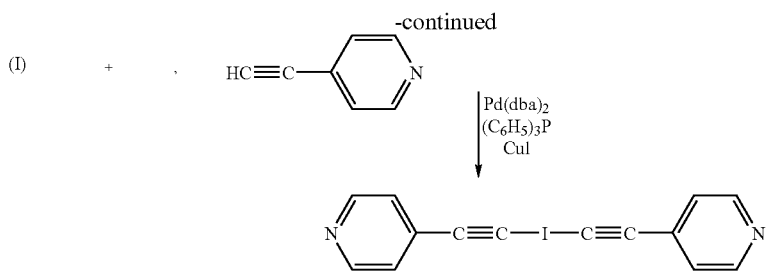

Example 12

Self-Assembly and Spectroscopic Ellipsometry Measurement

Differences in electrical conducting properties of the conducting molecules of the invention may be detected by measuring various spectroscopic and ellipsometric parameters. This example demonstrates various differences in those parameters in the compounds made and disclosed herein, indicating a variation in their electrical conduction.

The compounds used in this example are drawn from the previous examples. These compounds were subjected to self-assembly chemistry on gold, and silicon substrates. The Au substrates were thin films depositions on Si wafers with a Ti layer for adhesion. The Au substrate was further cleaned in a UV/ozone plasma cleaner.

The self-assembly was then prepared on the substrates using the procedures described in C. Zhou, et al, Appl. Phys. Lett. 71, 611, 1997; M. T. Cygan, et al, J. Am. Chem. Soc., 120, 2721-2732, 1998; and J. Chen, et al, Science, Vol 286, pg. 1550, 1999 Optical properties (index of refraction, "n" and extinction coefficient, "k") were determined from variable angle spectroscopic ellipsometry (VASE) at three incident angles covering the wavelength range from 143-800 nm, corresponding to an energy range of 1.5-8.67 eV. The samples for ellipsometry consisted of the self-assembled molecules on a gold-coated silicon wafer substrate. The VASE ellipsometer was manufactured by J. A. Woollam Company, 645 M Street, Suite 102, Lincoln, Nebr. 68508 USA. Optical constants were fit to these data simultaneously, using an optical model of the film on the substrate. This method is described in O, S. Heavens, Optical Properties of Thin Solid Films, pp. 55-62, Dover, N.Y., 1991.

Two approaches were used in the Ellipsometric modeling: a Cauchy (C) or a Spectral Cauchy (SC). In the Cauchy model fits, the index of refraction n of the self-assembled molecules was presumed to have a fixed value. Most typically n was set equal to 1.45, and then only the thickness of the self-assembled molecules was fitted. In the SC approach, the thickness found with the Cauchy model, was then fixed, and the optical constants, the complex index of refraction n+ik, was then fitted as a function of wave length. This allowed the determination of the spectral variation of the index of refraction and the extinction coefficient and gave a direct insight into the optical absorptions and electronic transitions in the self assembled molecules.

The results are shown in FIGS. 6-11, and below in Table 1. Hexane and Iodyne form insulating SAMs and were measured for comparison.

TABLE 1

| Molecule | X-ray Length | Ellips. Length | Electronic Transition Energies |
|---|---|---|---|
| Comp. Ex. 1: Hexadecane | 21.5 Å | 18.3 Å | — |
| Comp. Ex. 2: Lodyne | 13.8 Å | 5-6 Å | — |
| Ex. 9: PETB | 10.31 Å | 14.1 Å | 2.7 eV |
|  |  | 11.6 Å |  |
|  |  | 15.1 Å |  |
| Ex. 10: pF-PETB | 12.74 Å | 12.8 Å | 2.95 eV |
| Ex. 11: 3N-PETB | 21.87 Å | 12.8 Å | 4.1 eV |
| Ex. 12: 3-PETB | 21.87 Å | 70.3 Å | 4.0 eV |
| Ex. 13: 2F2NC3B | 21.73 Å | 35.0 Å | 6.3 eV |
|  |  |  | 7.2 eV |
|  |  |  | 7.6 eV Abs. Edge |

These data indicate that (a) the new compounds of the invention are indeed electrical conducting and (b) that the variations made in the placement and type of the various substituents resulted in changes in the electrical conductive properties of the compounds.

What is claimed is:

1. A conducting molecule selected from the group consisting of:

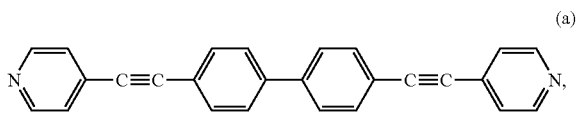

(a)

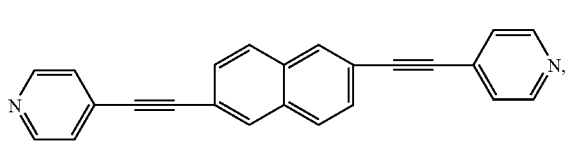

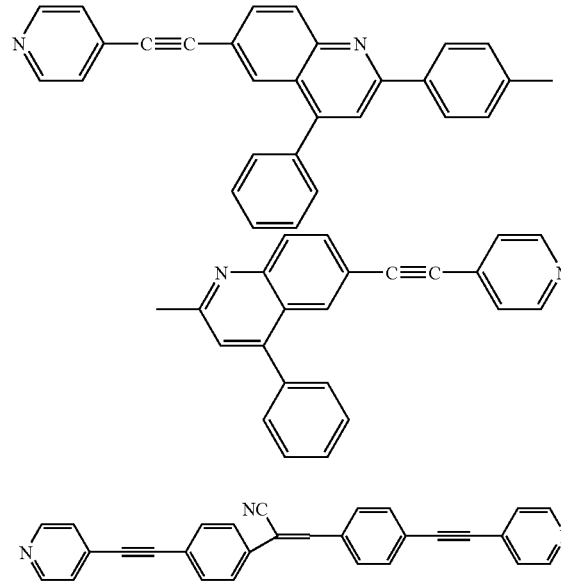
(c)
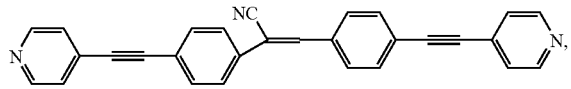
(d)
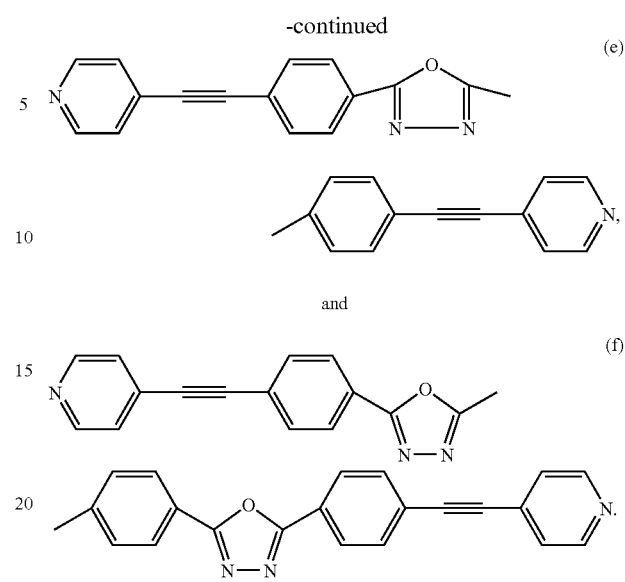
* * * * *

UNITED STATES PATENT AND TRADEMARK OFFICE
CERTIFICATE OF CORRECTION

PATENT NO. : 7,638,632 B2
APPLICATION NO. : 11/511934
DATED : December 29, 2009
INVENTOR(S) : French et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this

Ninth Day of November, 2010

David J. Kappos
*Director of the United States Patent and Trademark Office*